United States Patent [19]

Skurkovich et al.

[11] Patent Number: 4,898,184

[45] Date of Patent: Feb. 6, 1990

[54] MALE AND FEMALE CONDOMS FOR THE PREVENTION OF THE TRANSMISSION OF AIDS AND OTHER VENEREAL DESEASES

[76] Inventors: Boris Skurkovich, 18 Blaisdell Ave., Pawtucket, R.I. 02860; Simon Skurkovich, 802 Rollins Ave., Rockville, Md. 20852

[21] Appl. No.: 111,586

[22] Filed: Oct. 23, 1987

[51] Int. Cl.$^4$ .............................................. A61F 5/44
[52] U.S. Cl. .................................... 128/844; 128/917; 604/349
[58] Field of Search .................... 128/132 R, 891, 834, 128/835, 844, 840, 845; 604/349–353; 2/404, 407; 424/85; 514/841

[56] References Cited

U.S. PATENT DOCUMENTS

| D. 288,485 | 2/1987 | Denno | D24/51 |
|---|---|---|---|
| 2,548,149 | 4/1951 | Fowler, Jr. | 604/352 |
| 2,586,674 | 2/1952 | Lonne | 604/349 |
| 2,873,740 | 2/1959 | Wainwright | 604/349 |
| 3,212,500 | 10/1965 | Bardy . | |
| 3,363,624 | 1/1968 | Fishman | 604/349 |
| 3,508,550 | 4/1970 | Vollrath | 128/291 |
| 3,714,946 | 2/1973 | Rudes | 2/204 |
| 4,004,591 | 1/1977 | Freimark | 128/294 |
| 4,415,548 | 11/1983 | Reddy | 604/289 |
| 4,432,357 | 2/1984 | Pomeranz | 128/132 R |
| 4,446,860 | 5/1984 | Gutnick | 128/132 R |
| 4,664,104 | 5/1987 | Jaicks | 604/353 |
| 4,781,709 | 11/1988 | Grubman | 128/844 |
| 4,795,425 | 1/1989 | Pugh | 128/844 |
| 4,807,611 | 2/1989 | Johnson | 128/844 |

FOREIGN PATENT DOCUMENTS 0003173 7/1979 European Pat. Off. ............. 424/85

OTHER PUBLICATIONS

Outline for Successful Prophylactic Program, The Gee Bee Company, Waterbury, Conn. 16 pages, 1934.
Antisperm Antibodies in Infertility: The Role of Condom Therapy, Greentree M.D., Fertility and Sterility, vol. 37, No. 3, Mar. 1982, pp. 451 and 452.

*Primary Examiner*—Jerome L. Kruter
*Attorney, Agent, or Firm*—Wells & White

[57] ABSTRACT

Male and female condoms for the prevention of the transmission of AIDS and other venereal diseases are provided having an apron portion for covering the pubic area, thigh portion for covering the perineum and genitalia portions. Straps integral with the condom or adhesives are used to then hold the condoms in place.

12 Claims, 2 Drawing Sheets

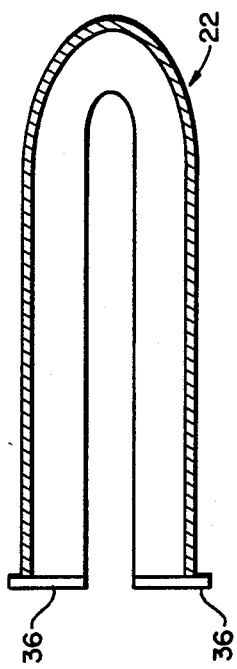
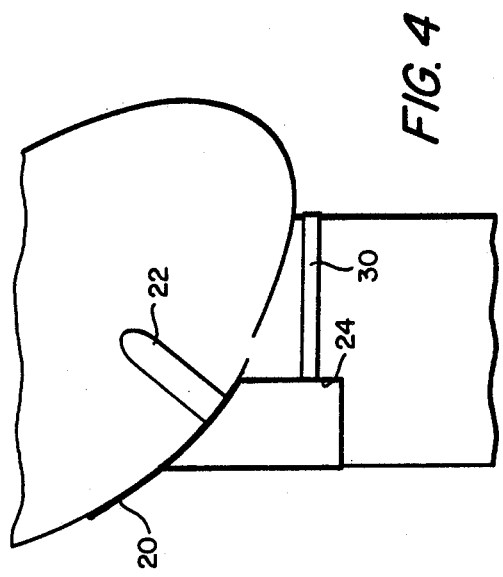
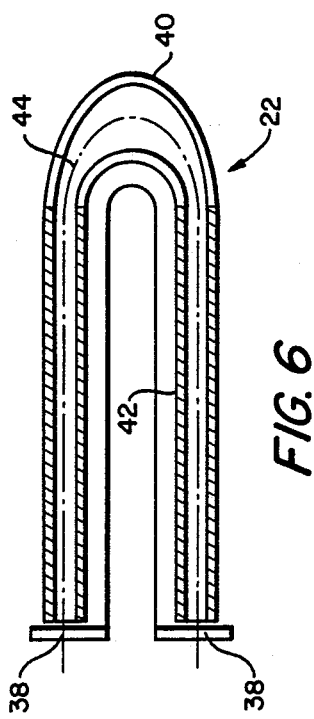
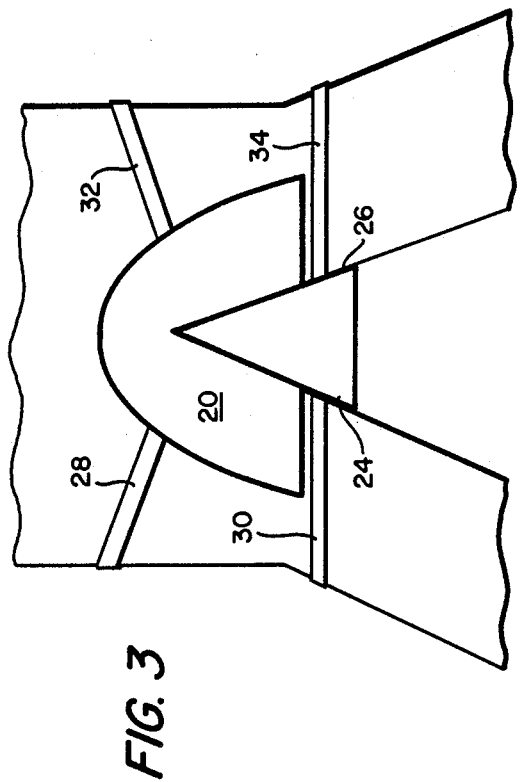

MALE AND FEMALE CONDOMS FOR THE PREVENTION OF THE TRANSMISSION OF AIDS AND OTHER VENEREAL DESEASES

BACKGROUND OF THE INVENTION

The field of the invention is medical genital receptacles for collecting discharge and the invention is particularly concerned with male and female condoms.

The state of the art may be ascertained by reference to U.S. Pat. Nos. 3,759,254; 4,415,548; 4,527,988 and 4,627,846 the disclosures of which are incorporated herein by reference.

Genital receptacles are used in the field of preventive medicine, and more particularly in the prevention of sexually transmitted diseases.

Currently, some of the more common sexually transmitted diseases are syphilis, gonorrhea, chlamydial infections, genital herpes simplex virus (HSV) infections, genital human papillomavirus (HPV) infections, hepatitis A infection, hepatitis B infection, cytomegalovirus infections, and acquired immunodeficiency syndrome (AIDS).

One of the modes of transmission of an infecting agent is its penetration of the body through inapparent breaks in abraded areas of the skin. Even microscopic breaks in the area of external genital organs, and also surrounding skin (such as the skin of the pubic area, inner thighs, and perineum) can serve as an entrance to the infecting agent. For example, chancre of primary syphilis appears at the site of inoculation of *Treponema pallidum* and chancres have been found on the skin surrounding genital areas. Similar modes of transmission are possible in other venereal diseases such as AIDS.

A method for prevention of sexually transmitted diseases is the use of condoms. Condoms that are available now cover only penis and scrotum thus leaving uncovered surrounding areas of the skin, such as pubic areas, perineum and inner surfaces of thighs. So, for example, condoms fail to prevent transmission of human immunodeficiency virus in up to 17% of the cases as disclosed by Fischl et al in "Evaluation of heterosexual partners, children, and household contacts of adults with AIDS," *JAMA*, Feb. 6, 1987—Vol. 257, No. 5, pages 640-644; Goedert JJ. "What is safe sex?" Sounding Board, in the *N Engl J Med* May 21, 1987-Vol 316, No. 21, pages 1339-1342.

SUMMARY OF THE INVENTION

Having in mind the limitations of the prior art it is an object of the present invention to provide new shapes and configurations of condoms which increase the chances of prophylaxis of venereal diseases, such as, for example, AIDS, syphilis, HSV, hepatitis A and B, and others.

Another object of the present invention is a condom for use by females.

Still another object of the present invention is a condom having a coating on the inside and/or outside surfaces thereof comprising agents which destroy spermatozoa.

Yet another object of the present invention is a condom having a coating on the inside and/or outside surfaces thereof which destroy infectious agents causing venereal diseases.

Agents which destroy spermatozoa and infectious agents are known from U.S. Pat. Nos. 4,415,548 and 4,527,988. A chemical ingredient is nonoxynol-9 which has been shown to inhibit human immunodeficiency virus (HIV) in vitro as disclosed by Hick, et al, in "Inactivation of HTL-III/LAV-infected cultures of normal human lymphocytes by nonoxynol-9 in vitro" as published by *The Lancet* Dec. 21/28, 1985—Vol. 2, pages 1422-1423.

Other agents which destroy spermatozoa and infectious agents include antibodies to spermatozoa, and to viruses and bacteria, respectively. These antibodies could be polyclonal as obtained from blood of people with high titers of antibodies to spermatozoa and/or viruses and bacteria, or from the blood of people and animals actively immunized with spermatozoa or their fragments and/or viral and bacterial antigens. These antibodies could also be monoclonal, obtained in human or mouse hybridomas.

Another embodiment of a male condom useful in achieving the objects of the present invention comprises a portion covering penis and integrally connected part in the elongated form of a triangle, covering the pubic area and lower abdomen. One of the possible ways to attach this triangular part to the skin of the lower abdomen is with the help of a narrow strip of glue-like material applied to the inner surface of the triangular part of the condom. This strip of glue can be covered with a strip of paper that is removed before use (analogous to the way envelopes are sealed). The other way to attach the triangular part is with the help of a thin belt which is an integral part of the condom, made out of the same material and attached to the superior part of the triangle covering the pubic area.

Another embodiment of the male condom consists of an elongated part covering the penis, and integrally connected with it a part (not in the form of a sack) which covers the scrotum, inner surfaces of thighs and perineum. It can be attached to the skin with the help of a weak glue (such as 3 M yellow papers) applied to the internal surface of the part covering thighs and perineum.

Yet another embodiment would combine all of the above features.

The embodiment of a female condom would be made of the same materials as a male condom which include films made from natural rubber latex and synthetic rubber latex as disclosed in U.S. Pat. No. 4,527,988.

An embodiment of the female condom comprises an elongated pat inserted into the vagina, and integrally connected with it a elongated part covering external genitalia, pubic, lower abdomen, inner thighs and perineum. It can be attached to the skin with the help of a weak glue applied to the internal surface of the parts covering the skin of the inner thighs, lower abdomen and perineum. The internal surface of the vaginal part of the condom could be made with small periodic elevations in order to simulate the natural surface of the vagina (so called vaginal columns).

One of the possible embodiments is to make the vaginal part of the condom out of two layers of material thus creating a cavity between them. This cavity can be filled with a small amount of liquid which could be heated within seconds to reach normal temperature of the vagina (between 36.5° C. and 38° C.). This is done in order to create more natural environment during coitus. This liquid could be heated either chemically, or with the help of a small battery having a thermopile.

The surface of the vaginal part of the condom, which is in contact with the mucous membranes of the vagina, could be covered with a weak glue.

The elongated part could be inserted into the vagina with the help of an elongated object and the external parts could be attached to the skin after that.

This female condom can also be used with a lubricant and/or a spermicide applied to the inner and/or outer surfaces of the vaginal part.

Another way to increase the temperature of the vaginal part of the condom is to warm up the elongated object used for the insertion of the vaginal part into the vagina (for example, it could be filled with warm water).

BRIEF DESCRIPTION OF THE DRAWINGS

The invention may best be described by reference to the accompanying drawings wherein:

FIG. 3 is a schematic front view of a female condom mounted in the genital area of a female human;

FIG. 4 is a side view of FIG. 3;

FIG. 5 is a detailed shown of the vaginal insertion portion of FIG. 4; and

FIG. 6 is a modified form of FIG. 5 having two layers of material wherein a heated liquid can be present.

DESCRIPTION OF THE PREFERRED EMBODIMENT

Figure 2:
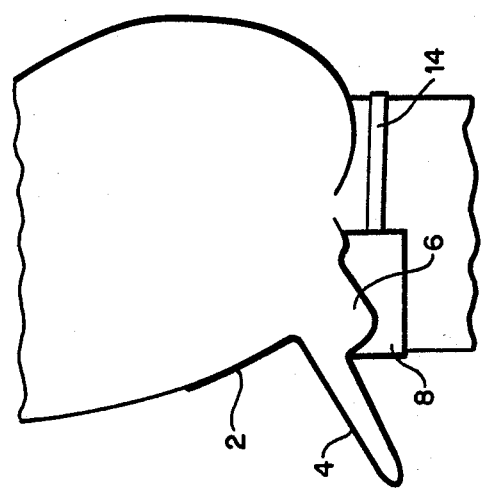
FIG. 2 is a side view of FIG. 1.
Figure 1:
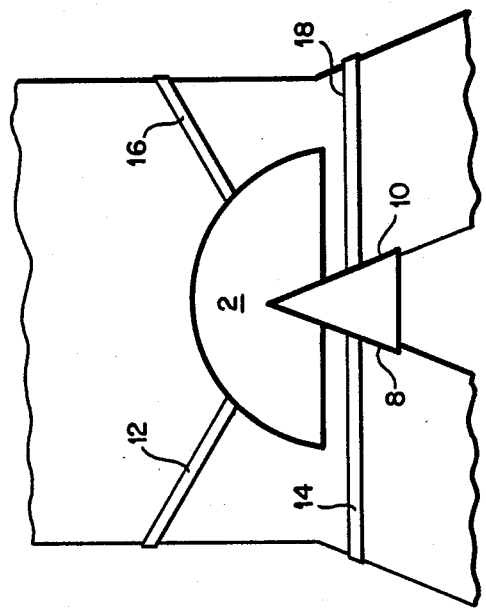
FIG. 1 is a schematic front view of a male condom mounted in the genital area of a male human.

With particular reference to FIGS. 1 and 2 the male condom is shown having an upper portion or apron 2 covering the lower abdomen and pubic area of a male human, a penis portion 4, a scrotum portion 6 and thigh portions 8 and 10 covering the perineum. Thin belt portions 12, 14, 16 and 18 are shown but it is understood that the thigh and pubic portions can be held in place by an adhesive.

FIGS. 3 and 6 show the female embodiments of the condom having an upper portion or apron 20 covering the lower abdomen and pubic area of a female human, a vaginal portion 22 and thigh portions 24 and 26. Thin belt portions 28, 30, 32 and 34 are integrally connected to the apron and thigh portions.

The vaginal portion 22 of FIG. 5 has a length of about 10 centimeters, an outer diameter of about 2 centimeters and an inner diameter of about 1.5 centimeters.

Thickened portions 36, 38 indicate the attachment surfaces of the vaginal portion with the apron portion.

FIG. 6 shows the vaginal portion having an outer surface 40, an inner surface 42 and liquid 44.

We claim:

1. A genital receptacle consisting essentially of a resilient and flexible unitary body construction of rubber latex having an apron portion adapted to cover the pubic area of a human, thigh portions adapted to cover the perineum area of a human and a genitalia portion adapted to cover the surfaces of the genitalia of a human, a spermicide on the outside thereof and said spermicide containing antibodies to viruses and bacteria.

2. The genital receptacle of claim 1, further comprising means for securing the receptacle to the surfaces of a human.

3. The genital receptacles of claim 2, wherein said means for securing is an adhesive.

4. The genital receptacle of claim 2, wherein said means for securing are straps integral with said construction.

5. The genital receptacle of claim 2, further comprising a spermicide coating on the inside thereof.

6. The genital receptacle of claim 1, wherein said genitalia portion is a vaginal portion with two layers defining a cavity adapted to receive a liquid.

7. A genital receptacle consisting essentially of a resilient and flexible unitary body construction of rubber latex having an apron portion adapted to cover the pubic area of a human, thigh portions adapted to cover the perineum area of a human and a genitalia portion adapted to cover the surfaces of the genitalia of a human, a spermicide on the outside thereof and said spermicide comprising antibodies to spermatozoa or their fragments.

8. The genital receptacle of claim 7, further comprising means for securing the receptacle to the surfaces of a human.

9. The genital receptacle of claim 8, wherein said means for securing is an adhesive.

10. The genital receptacle of claim 8, wherein said means for securing are straps integral with said construction.

11. The genital receptacle of claim 8, further comprising a spermicide coating on the inside thereof.

12. The genital receptacle of claim 7, wherein said genitalia portion is a vaginal portion with two layers defining a cavity adapted to receive a liquid.

* * * * *